(12) United States Patent
Hori

(10) Patent No.: US 9,945,657 B2
(45) Date of Patent: Apr. 17, 2018

(54) OPTICAL-COHERENCE-TOMOGRAPHY APPARATUS AND SURFACE-EMITTING LASER

(71) Applicant: CANON KABUSHIKI KAISHA, Tokyo (JP)

(72) Inventor: Yuichiro Hori, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/322,587

(22) PCT Filed: Jun. 22, 2015

(86) PCT No.: PCT/JP2015/003108
§ 371 (c)(1),
(2) Date: Dec. 28, 2016

(87) PCT Pub. No.: WO2016/002160
PCT Pub. Date: Jan. 7, 2016

(65) Prior Publication Data
US 2017/0138720 A1 May 18, 2017

(30) Foreign Application Priority Data
Jun. 30, 2014 (JP) ................. 2014-135391

(51) Int. Cl.
*H01S 5/18* (2006.01)
*G01B 9/02* (2006.01)
(Continued)

(52) U.S. Cl.
CPC ..... *G01B 9/02069* (2013.01); *G01B 9/02004* (2013.01); *G01B 9/0207* (2013.01);
(Continued)

(58) Field of Classification Search
CPC ............ G01B 9/02091; G01B 9/02004; G01B 9/02002; G01B 9/02069; H01S 5/18; H01S 5/183
See application file for complete search history.

(56) References Cited

U.S. PATENT DOCUMENTS

| 2014/0028997 A1* | 1/2014 | Cable ................. G01B 9/02091 356/51 |
| 2014/0104618 A1* | 4/2014 | Potsaid ................ G02B 26/105 356/497 |
| 2015/0110295 A1* | 4/2015 | Jenkner ................... H04R 1/08 381/114 |

FOREIGN PATENT DOCUMENTS

| JP | 2008046452 A1 | 2/2008 |
| WO | 2014018950 A1 | 1/2014 |
| WO | 2014023777 A2 | 2/2014 |

OTHER PUBLICATIONS

Benjamin Potsaid et al, MEMS tunable VCSEL light source for ultrahigh speed 60kHz—1MHz axial scan rate and long range centimeter class OCT imaging, Proc of SPIE vol. 8213, pp. 82130M-1-82130M-8, 2012.

* cited by examiner

*Primary Examiner* — Jonathan Hansen
(74) *Attorney, Agent, or Firm* — Canon U.S.A., Inc. IP Division

(57) ABSTRACT

An optical-coherence-tomography apparatus includes a light-source unit configured to emit light while changing a wavelength of the light; an optical interferometric system configured to split the light from the light-source unit into illuminating light to be applied to an object and reference light, and to generate interfering light from the illuminating light reflected by the object and the reference light; a photodetection unit configured to receive the interfering light, and an information-acquiring unit configured to
(Continued)

acquire information on the object from the interfering light received by the photodetection unit. The light-source unit performs wavelength sweep by displacing a movable portion with an electrostatic force generated with the application of a voltage. The optical-coherence-tomography apparatus further includes a pull-in-detection unit configured to detect whether or not a pull-in effect is occurring on the movable portion of the light-source unit.

17 Claims, 9 Drawing Sheets

(51) Int. Cl.
*H01S 5/0683* (2006.01)
*H01S 5/183* (2006.01)
*H01S 5/06* (2006.01)
*H01S 5/04* (2006.01)
*H01S 5/042* (2006.01)

(52) U.S. Cl.
CPC .......... *G01B 9/02091* (2013.01); *H01S 5/041* (2013.01); *H01S 5/042* (2013.01); *H01S 5/0607* (2013.01); *H01S 5/06837* (2013.01); *H01S 5/183* (2013.01)

[Fig. 1]
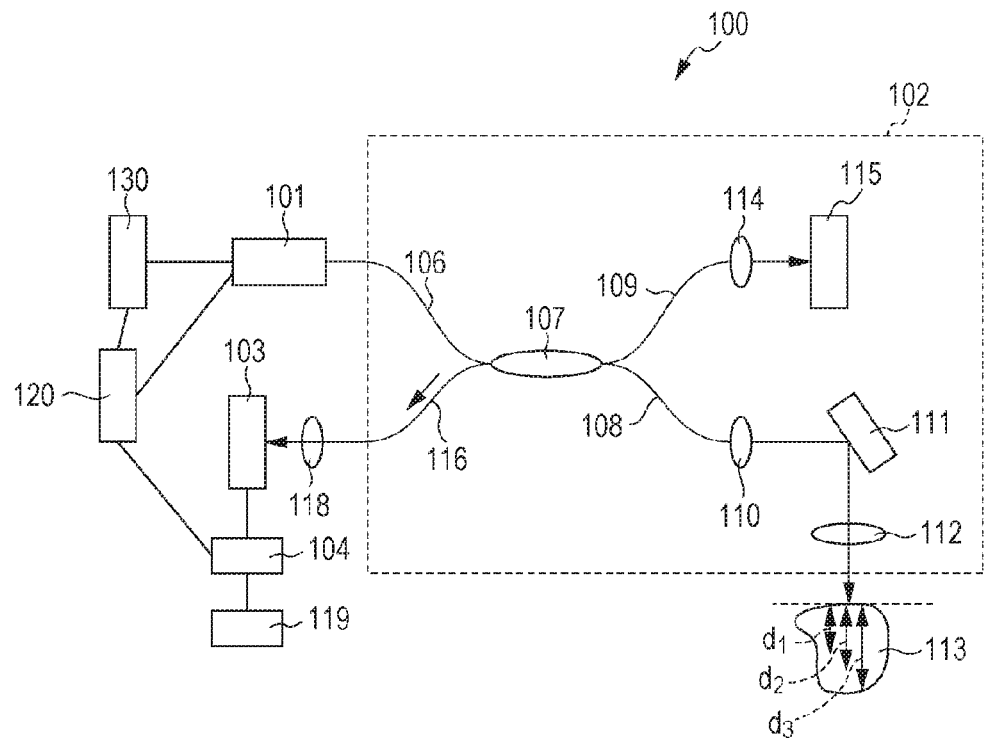
[Fig. 2]
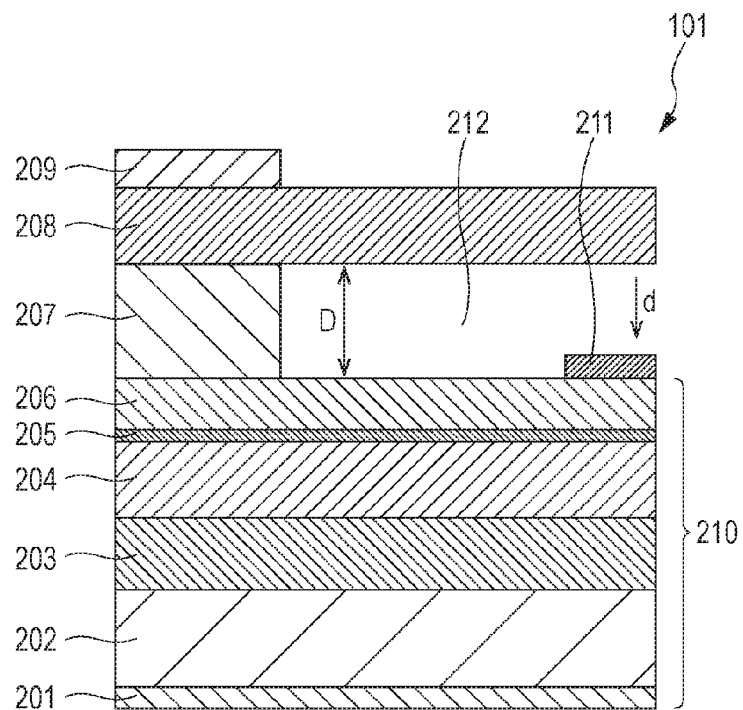

[Fig. 3]
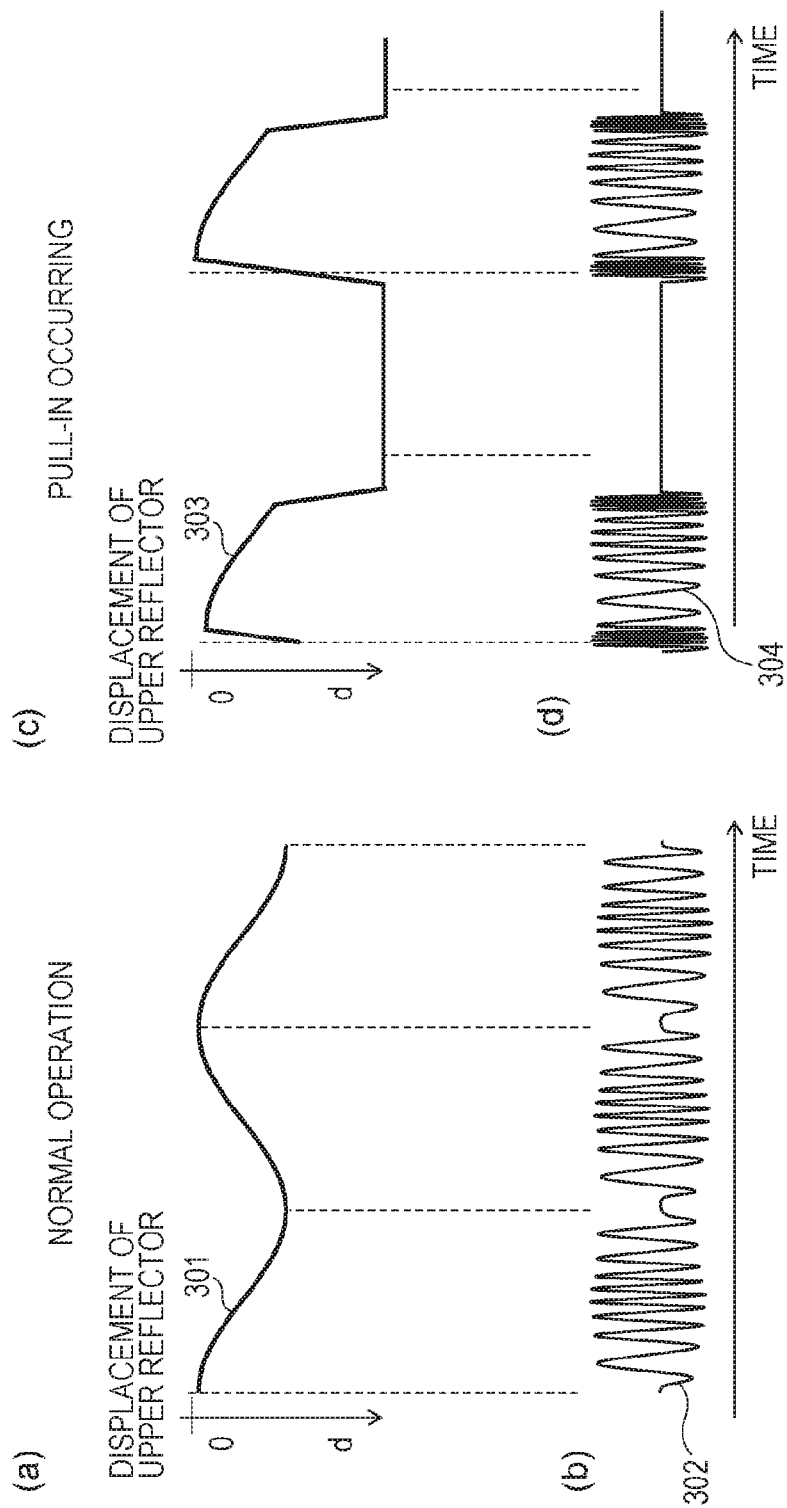

[Fig. 4]
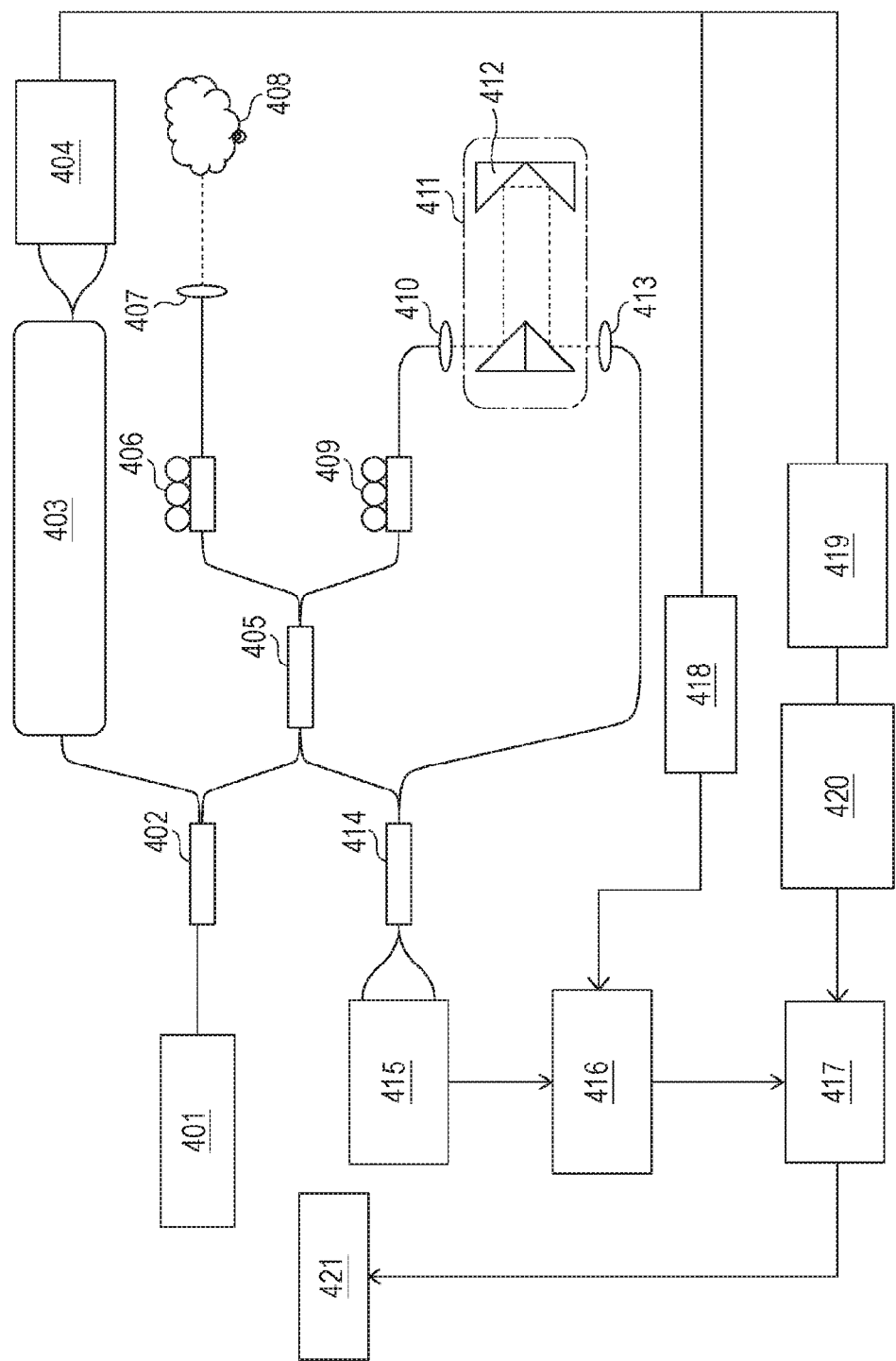

[Fig. 5]
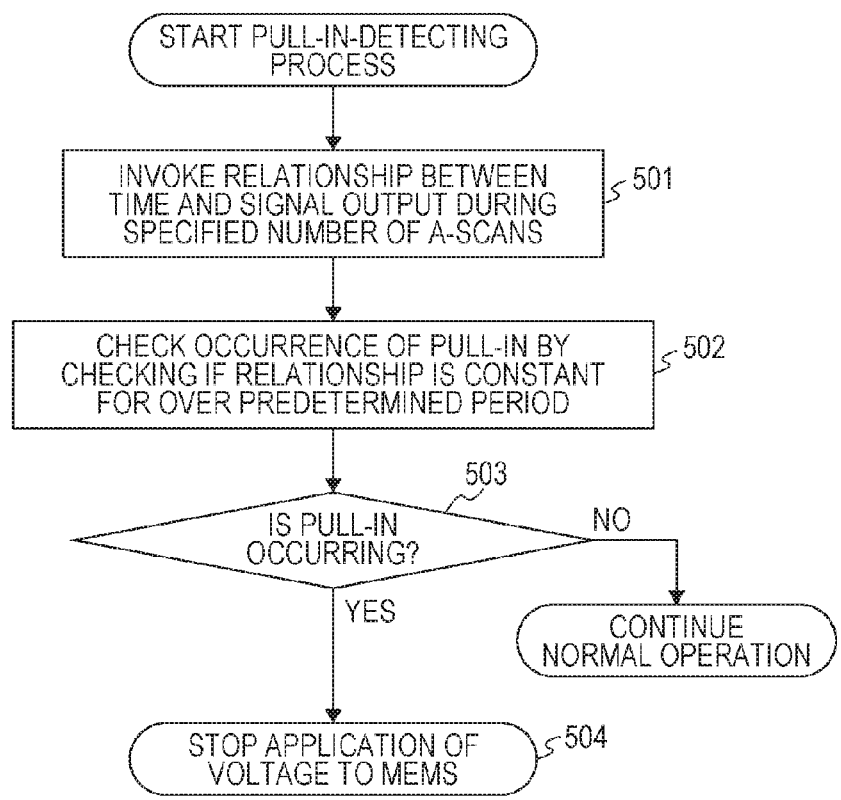

[Fig. 6]
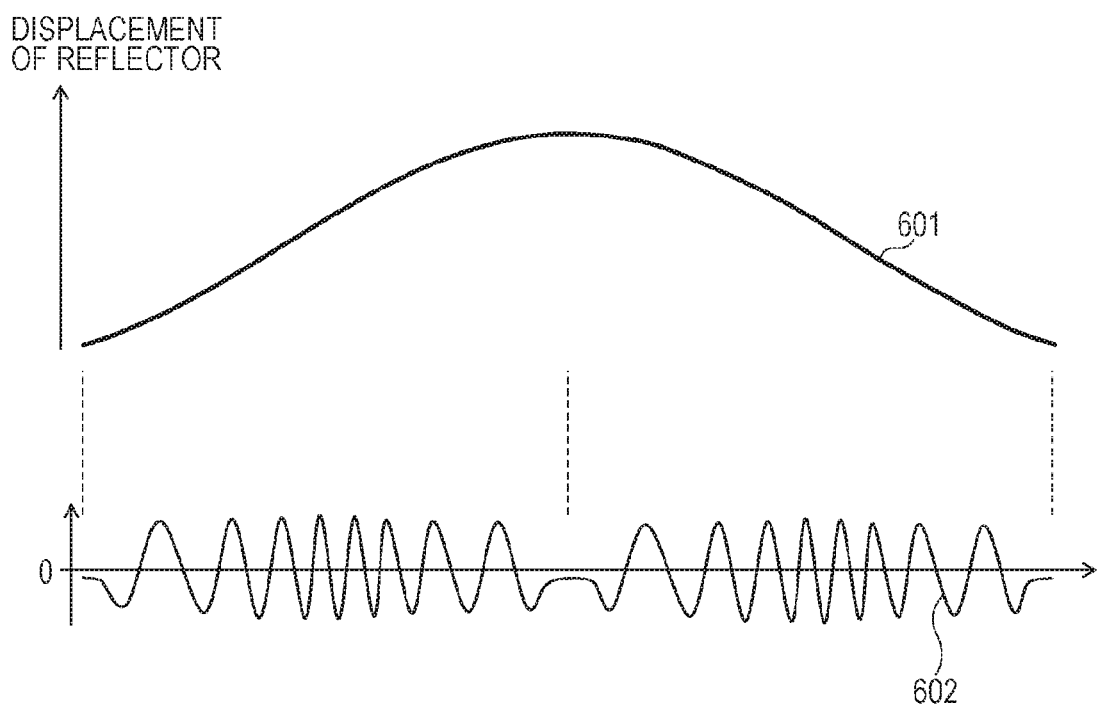

[Fig. 7]
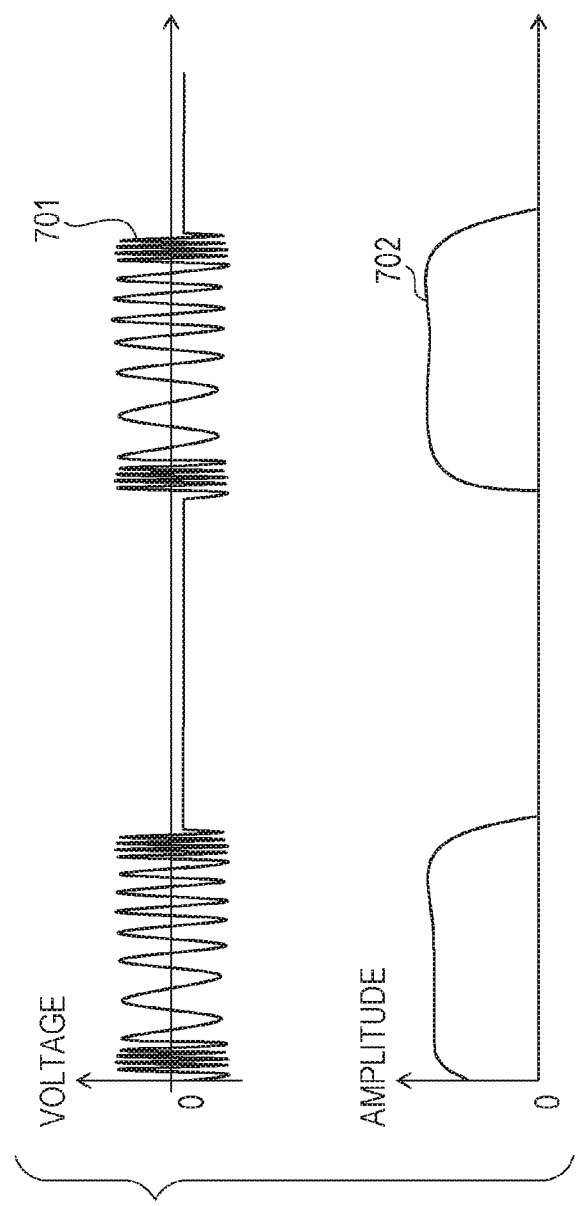

[Fig. 8]
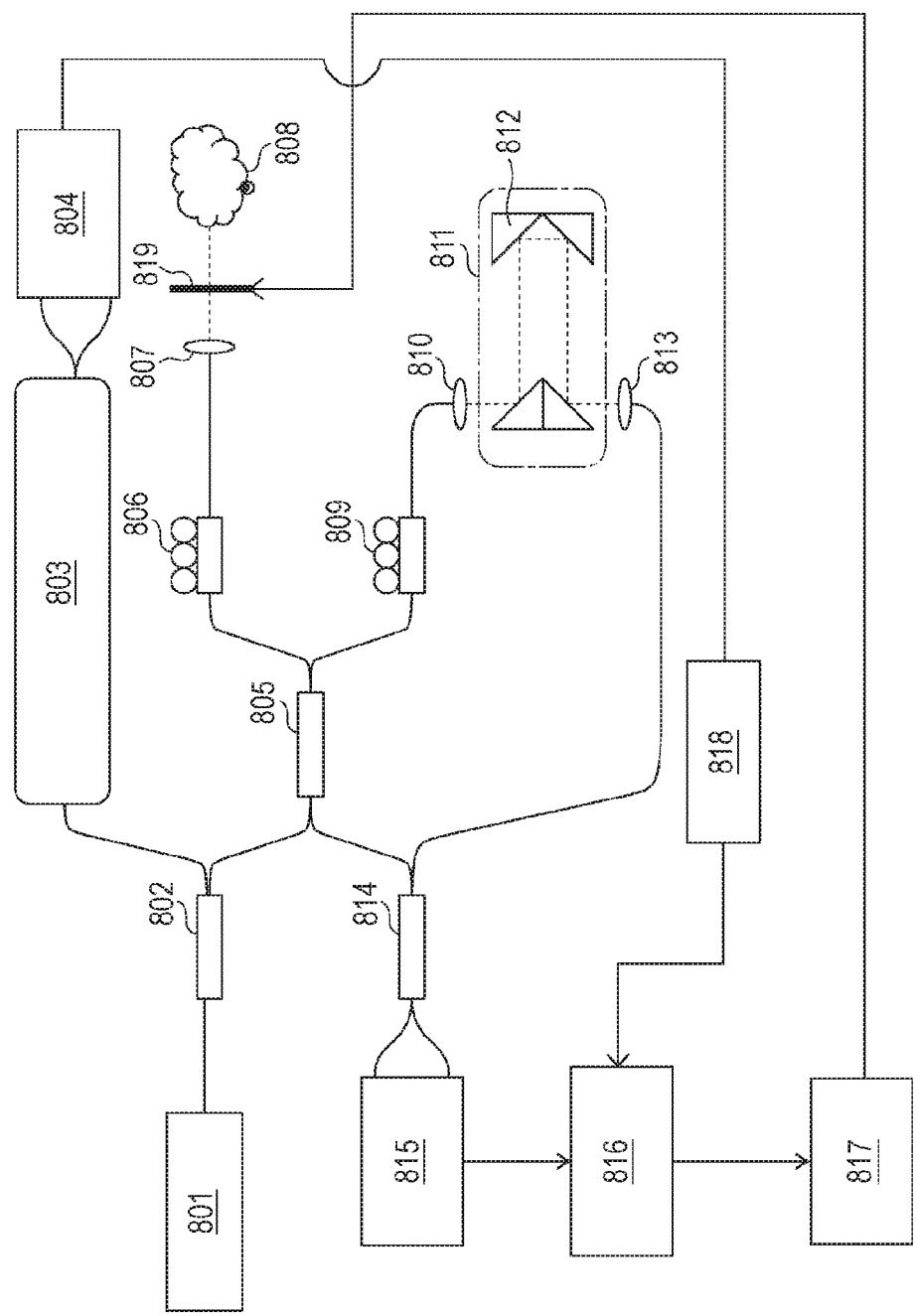

[Fig. 9]
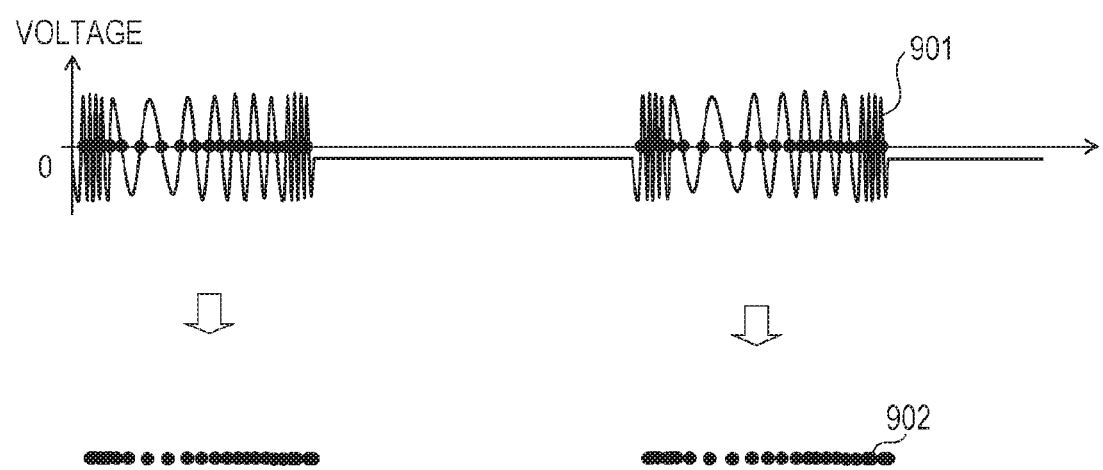

[Fig. 10]
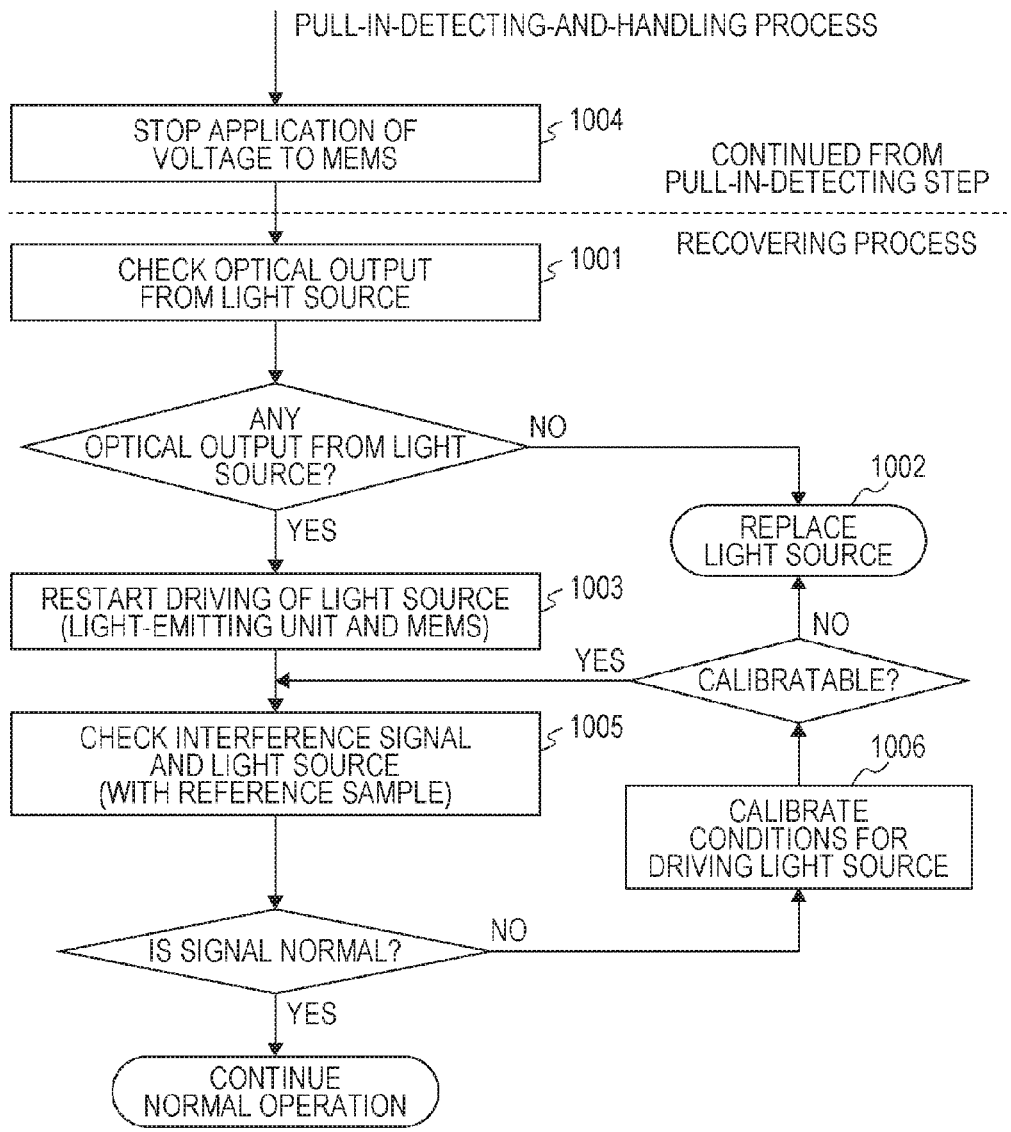

OPTICAL-COHERENCE-TOMOGRAPHY APPARATUS AND SURFACE-EMITTING LASER

TECHNICAL FIELD

The present invention relates to an optical-coherence-tomography apparatus that is capable of detecting the occurrence of a pull-in effect, and a surface-emitting laser,

BACKGROUND ART

In recent years, research and development of optical coherence tomography (hereinafter occasionally abbreviated to OCT) has been underway energetically in various fields including the medical field.

An OCT technique employing a wavelength-variable light source is called swept-source OCT (abbreviated to SS-OCT). The SS-OCT technique is superior to other techniques in terms of high speed, a large signal-to-noise (S/N) ratio, and so forth and is expected to develop further.

Known wavelength-variable light sources include a vertical-cavity surface-emitting laser (abbreviated to VCSEL), which is hereinafter occasionally referred to as wavelength-variable VCSEL.

A known wavelength-variable VCSEL includes a microelectromechanical system (abbreviated to MEMS) functioning as a movable unit for varying the wavelength. The movable unit includes a mirror functioning as a component of a resonator. By displacing the movable unit with an electrostatic force, the length of the resonator is changed, whereby the wavelength of light emitted from the VCSEL is changed (NPL 1).

CITATION LIST

Non Patent Literature

NPL 1: Proceedings of SPIE Vol. 8213, 82130M-1-M-8 (2012)

SUMMARY OF INVENTION

Technical Problem

When a driving voltage higher than a certain level is applied to the electrostatically driven MEMS of the wavelength-variable light source, one of electrodes that drive the MEMS is abruptly pulled toward and comes into contact with the other driving electrode, which is known as a pull-in effect. The electrodes that drive the MEMS are hereinafter occasionally referred to as MEMS electrodes. If the pull-in effect occurs in an OCT apparatus including a wavelength-variable light source, the wavelength of the light from the light source abruptly changes during wavelength sweep, which may disturb the acquisition of data on a measurement object. Moreover, if the light source is a laser that emits light with the injection of an electric current thereinto, a high current flows from the MEMS electrodes into a light-emitting portion of the laser, leading to possible emission of high-intensity light.

Solution to Problem

According to an aspect of the present invention, there is provided an optical-coherence-tomography apparatus including a light-source unit configured to emit light while changing a wavelength of the light; an optical interferometric system configured to split the light from the light-source unit into illuminating light to be applied to an object and reference light, and to generate interfering light from the illuminating light reflected by the object and the reference light; a photodetection unit configured to receive the interfering light; and an information-acquiring unit configured to acquire information on the object from the interfering light received by the photodetection unit. The light-source unit performs wavelength sweep by displacing a movable portion with an electrostatic force generated with the application of a voltage. The optical-coherence-tomography apparatus further includes a pull-in-detection unit configured to detect whether or not a pull-in effect is occurring on the movable portion of the light-source unit.

Further features of the present invention will become apparent from the following description of exemplary embodiments with reference to the attached drawings.

BRIEF DESCRIPTION OF DRAWINGS

FIG. 1 is a schematic diagram of an optical-coherence-tomography (OCT) apparatus according to a first embodiment of the present invention.

FIG. 2 is a schematic diagram illustrating a light-source unit according to the first embodiment of the present invention.

FIG. 3 includes charts illustrating the amount of displacement of a movable portion (an upper reflector) and an interference signal generated by a clock-generating unit.

FIG. 4 is a schematic diagram of an OCT apparatus according to a second embodiment of the present invention.

FIG. 5 is a flowchart illustrating a process of detecting and handling a pull-in effect according to the second embodiment of the present invention.

FIG. 6 is a conceptual chart illustrating the displacement of the reflector and data generated by a clock-generating unit that are observed during one period of driving of a MEMS reflector according to the second embodiment of the present invention.

FIG. 7 is a conceptual chart for explaining how to read data outputted from a clock-generating unit that is used in checking the occurrence of the pull-in effect in a third embodiment of the present invention.

FIG. 8 is a schematic diagram of an OCT apparatus according to a fifth embodiment of the present invention.

FIG. 9 is a conceptual chart for explaining how to read data outputted from a clock-generating unit that is used in checking the occurrence of the pull-in effect in the fifth embodiment of the present invention.

FIG. 10 is a flowchart illustrating a process of recovery from a state where the occurrence of the pull-in effect has been detected according to a sixth embodiment of the present invention.

DESCRIPTION OF EMBODIMENTS

First Embodiment

An optical-coherence-tomography (OCT) apparatus according to a first embodiment of the present invention will now be described.

OCT Apparatus

An OCT apparatus 100 according to the first embodiment will now be described with reference to FIG. 1. Arrows illustrated in FIG. 1 each represent a direction in which light travels.

The OCT apparatus 100 according to the first embodiment includes at least a light-source unit 101, an optical interferometric system 102, a photodetection unit 103, and an information-acquiring unit 104. The information-acquiring unit 104 acquires information on an object 113 to be measured. The information-acquiring unit 104 includes a Fourier transform device. The Fourier transform device included in the information-acquiring unit 104 may be provided in any form, as long as the information-acquiring unit 104 has a function of performing Fourier transform on data inputted thereto. The first embodiment concerns an exemplary case where the information-acquiring unit 104 includes an arithmetic device, and the arithmetic device has a function of performing Fourier transform. Specifically, the arithmetic device is a computer including a central processing unit (CPU), and the computer includes an application for performing Fourier transform. Another possible case is that the information-acquiring unit 104 includes a Fourier-transform circuit having a function of performing Fourier transform.

Light emitted from the light-source unit 101 travels through the optical interferometric system 102, and is outputted as interfering light carrying information on the object 113 to be measured. The interfering light is received by the photodetection unit 103. The photodetection unit 103 may be a balanced photodetector or a simple intensity-monitoring device. The interfering light is received at regular wave-number intervals. Information on a temporal waveform representing the intensity of the interfering light is transmitted from the photodetection unit 103 to the information-acquiring unit 104.

To allow the information-acquiring unit 104 to sample the interfering light at regular wave-number intervals, the OCT apparatus 100 according to the first embodiment includes a clock-generating unit 120 that detects the timing of sampling to be performed at the regular wave-number intervals. The clock-generating unit 120 derives a portion of the light emitted from the light-source unit 101 and, from the portion of the light, acquires an interference signal having peaks appearing at regular wave-number intervals. On the basis of the interference signal, the clock-generating unit 120 generates a clock signal that pulsates at the regular wave-number intervals. The clock signal is transmitted to the information-acquiring unit 104.

The information-acquiring unit 104 that has acquired the information on the intensity of the interfering light performs Fourier transform on the information, thereby acquiring information on the object 113 (for example, information on the object 113 in the form of a tomographic image). Elements other than the light-source unit 101, the optical interferometric system 102, the photodetection unit 103, the information-acquiring unit 104, and a pull-in-detection unit 130 may be provided arbitrarily within the scope of the present invention. If the information-acquiring unit 104 does not have any Fourier transform device, information on the object 113 may be acquired by a maximum entropy method (MEM).

Now, a process of acquiring information, in the form of a tomographic image, on the object 113 to be measured with light emitted from the light-source unit 101 will be described in detail.

Light emitted from the light-source unit 101 capable of changing the wavelength of the light travels through a fiber 106 and enters a coupler 107, where the light is split into illuminating light that is fed into an illuminating-light fiber 108 and reference light that is fed into a reference-light fiber 109. The illuminating light travels through a collimator 110, thereby turning into collimated light. The collimated light is then reflected by a mirror 111. The light reflected by the mirror 111 travels through a lens 112, falls onto the object 113, and is reflected by each of different layers at respective depths of the object 113. Meanwhile, the reference light travels through a collimator 114 and is reflected by a mirror 115. In the coupler 107, the light reflected by the object 113 and the light reflected by the mirror 115 interfere with each other into interfering light. The interfering light travels through a fiber 116 and a lens 118, is received by the photodetection unit 103, and enters the information-acquiring unit 104, where the interfering light undergoes Fourier transform. Thus, information on the object 113 in the form of a tomographic image is acquired. The values obtained by Fourier transform correspond to the difference between the lengths of two optical paths, which are an optical path of the light emitted from the coupler 107 and returning to the coupler 107 after being reflected by a corresponding one of the layers of the object 113, and an optical path of the light emitted from the coupler 107 and returning to the coupler 107 after being reflected by the mirror 115. Hence, the information on the object 113 in the form of a tomographic image represents, for example, the relationship between each of depths ($d_1$, $d_2$, and $d_3$) from the surface of the object 113 to the respective layers of the object 113 and the intensity of light reflected by a corresponding one of the layers of the object 113.

The information on the object 113 in the form of a tomographic image may be transmitted from the information-acquiring unit 104 to an image display unit 119 so that the tomographic image can be displayed thereon. If the mirror 111 is operated such that the illuminating light is scanningly moved in a plane perpendicular to the direction of incidence of the illuminating light on the object 113, a three-dimensional tomographic image of the object 113 is acquired.

The OCT apparatus 100 according to the first embodiment includes the pull-in-detection unit 130 that detects the occurrence of the pull-in effect in the light-source unit 101. In the first embodiment, the pull-in-detection unit 130 detects the occurrence of the pull-in effect on the basis of the clock signal generated by the clock-generating unit 120.

Description of Pull-In Effect

A specific method of detecting the occurrence of the pull-in effect according to the first embodiment will now be described, taking an exemplary case where the light-source unit 101 is a wavelength-variable VCSEL including a MEMS (hereinafter occasionally referred to as MEMS-VCSEL) illustrated in FIG. 2.

Pull-In Effect

The pull-in effect will first be described in detail.

The MEMS-VCSEL according to the first embodiment includes a half VCSEL 210 in which a lower electrode 201, a substrate 202, a lower reflector 203, a lower cladding layer 204, an active layer 205, and an upper cladding layer 206 are stacked in that order.

An insulating layer 207, an upper reflector 208, and an upper electrode 209 are stacked in that order on the upper cladding layer 206. Furthermore, a common electrode 211 is provided on the upper cladding layer 206. The common electrode 211 and the lower electrode 201 in combination inject an electric current into the active layer 205, whereby the active layer 205 emits light, and laser oscillation occurs in which the upper reflector 208 and the lower reflector 203 that form a resonator resonate with each other. In the first embodiment, the laser light emitted through the upper reflector 208 is used for the OCT measurement.

The length of an air gap 212 from the interface between the upper cladding layer 206 and the air gap 212 to the interface between the upper reflector 208 and the air gap 212 is defined as a distance D (also referred to as air-gap length). When the distance D changes, the length of the resonator changes. As a result of a change in the length of the resonator, the wavelength of the light emitted changes. The wavelength of the oscillation is changeable by changing the optical-axis-direction position of not only the upper reflector 208 alone but also at least one of the upper reflector 208 and the lower reflector 203.

The first embodiment concerns a MEMS as the upper reflector 208 provided in the form of a cantilever as illustrated in FIG. 2. Specifically, when a voltage is applied between the upper electrode 209 and the common electrode 211, an electrostatic force is generated between the upper reflector 208, which is a movable portion, and the upper cladding layer 206, whereby the upper reflector 208 is displaced in such a manner as to be pulled toward the upper cladding layer 206 (in a direction represented by an arrow d). In the first embodiment, the upper reflector 208 itself is provided in the form of a cantilever. Alternatively, a semiconductor cantilever upon which an upper reflector is provided may be employed. While the MEMS according to the first embodiment is of a cantilever type in which one end of a beam is supported, a MEMS in the form of a doubly supported beam two ends of which are supported may alternatively be employed. In the latter case also, the problem of the pull-in effect addressed in the present invention occurs likewise.

In a MEMS in which the movable portion is displaced with an electrostatic force, the following problem may arise. When a voltage that makes the distance D a certain length or shorter is applied between the movable portion (the upper reflector) and the upper cladding layer, the movable portion is abruptly pulled toward and comes into close contact with the upper cladding layer. Such a phenomenon is called a pull-in effect. It is known that, for example, in a case where an unmodulated static voltage is applied between simple flat plate-like members extending parallel to each other, the certain length (hereinafter referred to as critical gap), which varies with the shape and other factors of the MEMS, is ⅔ of the initial distance established when no voltage is applied (the voltage in such a case is referred to as pull-in voltage). That is, letting the distance D established when no voltage is applied be X, the pull-in effect occurs if any voltage is applied and the distance D is reduced to 2X/3 or shorter.

The pull-in effect may trigger some unfavorable situations. For example, if the upper reflector is abruptly pulled toward the upper cladding layer, the wavelength changes abruptly. Subsequently, if the upper reflector comes into close contact with the upper cladding layer, the wavelength stops changing. Hence, if such a MEMS-VCSEL is used as a light source of an OCT apparatus, the acquisition of data on the measurement object may be interrupted. Consequently, the range of wavelength that can be acquired may be narrowed, leading to possible problems such as a reduction in the resolution of the resulting OCT image. For another example, in a case where the active layer emits light with the injection of an electric current thereinto as in the first embodiment, if the upper reflector comes into close contact with the upper cladding layer, an electrical short circuit occurs and a high current may be injected into the active layer. Consequently, a highly intense light may be outputted from the MEMS-VCSEL, and the highly intense light may be applied to the examinee through the OCT apparatus. According to the first embodiment, the occurrence of the pull-in effect is detectable. Furthermore, if the occurrence of the pull-in effect is detected, such a state affected by the pull-in effect can be changed to a state free of the pull-in effect or the influence of the pull-in effect upon the OCT data can be suppressed.

Principle of Detection of Pull-in Effect

FIG. 3 includes charts illustrating the amount of displacement of the movable portion (the upper reflector 208) over time (illustrated in each of parts (a) and (c)) and the interference signal generated in the clock-generating unit (illustrated in each of parts (b) and (d)) in a case where the upper reflector 208 is in normal operation (free of the pull-in effect) and in a case where the pull-in effect is occurring on the upper reflector 208. The clock-generating unit 120 according to the first embodiment acquires the interference signal, for example, from a Fabry-Perot interferometer in the unit. Peaks of the interference signal appear at regular wave-number intervals. Hence, the clock-generating unit 120 can generate a clock signal that pulsates at regular wave-number intervals by transmitting the clock signal in accordance with the peaks of the interference signal. The vertical axis, denoted by d, of each of the charts illustrated in parts (a) and (c) of FIG. 3 represents the amount of displacement of the upper reflector 208 toward the upper cladding layer 206 at the application of a voltage, with the initial position of the upper reflector 208 that is yet to be displaced being defined as zero. In the first embodiment, points of the interference signal that are observed at regular wave-number intervals are regarded as the respective peaks of the interference signal. Alternatively, points of the interference signal that are observed at regular wave-number intervals may be regarded as points at each of which the amplitude (intensity) of the interference signal is zero.

Hereinafter, a case where the upper reflector 208 is sinusoidally driven at a frequency lower than the resonance frequency will be discussed.

In the normal operation, referring to part (a) in FIG. 3, the upper reflector 208 is displaced sinusoidally as represented by a curve 301, following the sinusoidal voltage applied thereto. In this case, the interference signal is represented by a wave 302 whose period is short when the speed of displacement of the upper reflector 208 is high (when the gradient of the curve 301 is steep) and is long when the speed of displacement of the upper reflector 208 is low. At the peak or bottom of the curve 301 where the speed of displacement of the upper reflector 208 is lowest (at a point where the amount of displacement is largest or smallest), the period of the interference signal is longest.

Referring to part (c) of FIG. 3, while the pull-in effect is not occurring, the upper reflector 208 is displaced sinusoidally. However, if the upper reflector 208 is significantly displaced and the distance D to the half VCSEL 210 becomes smaller than the critical gap, the pull-in effect occurs and the upper reflector 208 is abruptly pulled toward the half VCSEL 210. Once the upper reflector 208 (or the cantilever including the upper reflector 208, which is also hereinafter referred to as the upper reflector 208) is pulled toward the half VCSEL 210, the upper reflector 208 is theoretically kept in close contact with the half VCSEL 210 until the voltage applied between the upper electrode 209 and the common electrode 211 intended for driving the MEMS is reduced to zero.

If the upper reflector 208 is displaced as represented by a curve 303, the interference signal is correspondingly represented by a wave 304 illustrated in part (d) of FIG. 3. While the upper reflector 208 is displaced sinusoidally, the period of the interference signal 304 is the same as that observed in the normal operation. However, when the pull-in effect occurs, the speed of displacement of the upper reflector 208 increases. Accordingly, the period of the interference signal is shortened. Once the upper reflector 208 comes into close contact with the half VCSEL 210, the wavelength of the light emitted from the MEMS-VCSEL remains unchanged, that is, the interference signal becomes constant. Subsequently, when the voltage that has been applied is reduced to zero, the upper reflector 208 starts to displace sinusoidally again. Hence, detecting a situation where the intensity of the interference signal is constant for a period of time longer than in the normal operation is regarded as detecting the occurrence of the pull-in effect. This detection method also applies to the clock signal. That is, the occurrence of the pull-in effect can be detected by detecting a situation where the intensity of the clock signal is constant.

If the MEMS is driven at a frequency higher than or equal to the resonance frequency, the pull-in voltage and the size of the critical gap are different from those described above, because the way of displacement of the movable portion at the application of a voltage and the phase of the voltage applied are different from those described above. Accordingly, the conditions that cause the pull-in effect and the pattern of the interference signal are different from those in the case illustrated in FIG. 3. Even in that case, the pull-in effect can be detected in the same manner as described above, that is, by detecting a situation where the interference signal or the clock signal is constant for a certain period of time.

In a case where a certain bias voltage is applied to the MEMS in addition to the sinusoidal driving voltage, the upper reflector 208 does not go out of contact with the half VCSEL 210 and the pull-in effect is not eliminated, unlike the case of the first embodiment. Even in such a case, the pull-in effect can be detected in the same manner as described above, that is, by detecting a situation where the interference signal or the clock signal is constant for a certain period of time.

There are several methods of detecting the occurrence of the pull-in effect by detecting a situation where the interference signal or the clock signal is constant for a certain period of time. First, focusing on the fact that the intensity of the interference signal is constant while the pull-in effect is occurring, a situation where the value representing the intensity of the interference signal is constant at a certain value for a predetermined period of time or longer may be detected. Alternatively, assuming that the interference signal is a periodic signal whose period is variable, a situation where the amplitude of the periodic signal is at a predetermined value or smaller (for example, zero) for a longer time than a predetermined period of time may be detected. Alternatively, a situation where the interval between pulses of the clock signal is longer than a predetermined interval may be detected.

Alternatively, focusing on the fact that the value of the interference signal generated by the clock-generating unit 120 remains unchanged while the pull-in effect is occurring, the pull-in effect may be detected by detecting a situation where the derivative of the interference signal is zero for a longer time than a certain period of time.

Instead of the above method of detecting a situation where the intensity of the interference signal or the clock signal is constant at a certain value for a longer time than a certain period of time, a situation where the period of the signal becomes shorter before becoming constant at a certain value may be detected. Alternatively, a combination of a situation where the period of the signal becomes shorter and a subsequent situation where the signal becomes constant at a certain value may be detected.

The above methods of detecting the pull-in effect may each be implemented solely, or two or more of the methods may be combined. The values of "a certain period of time" and "a certain value" are each not necessarily exactly the same in all cases, and may each include some margin within the range in which the advantageous effects of the present invention are produced. While the first embodiment concerns a case where the pull-in-detection unit 130 detects the occurrence of the pull-in effect on the basis of the output from the clock-generating unit 120, the present invention is not limited to such a case.

Pull-In-Detection Unit

The pull-in-detection unit 130 according to the first embodiment is not specifically limited as long as it is capable of detecting the occurrence of the pull-in effect and, if the occurrence of the pull-in effect is detected, transmitting a signal. For example, the pull-in-detection unit 130 may include a photodetector (PD) that detects the interference signal or the clock signal as described above, and a signal-transmitter that transmits a signal on the basis of the intensity of light detected by the photodetector.

If the pull-in-detection unit 130 has detected the occurrence of the pull-in effect, the pull-in-detection unit 130 may transmit a signal to a pull-in-handling unit described below.

Pull-In-Handling Unit

The OCT apparatus 100 according to the first embodiment may include a pull-in-handling unit that performs a control operation which eliminates the pull-in effect at the receipt of the signal notifying the occurrence of the pull-in effect from the pull-in-detection unit 130, or changes any unfavorable situation for the acquisition of an OCT image to a favorable situation.

According to the first embodiment, the pull-in-handling unit can implement several methods of handling the pull-in effect.

First, to eliminate the pull-in effect, the voltage applied to the electrodes that drive the MEMS may be reduced to zero, for example. Such a solution is effective in terms of eliminating the pull-in effect fundamentally. After the voltage is reduced to zero, the voltage may be set to a lower level than the level at which the pull-in effect has occurred. Thus, the MEMS can be driven at a voltage that is less likely to cause the pull-in effect.

The OCT apparatus 100 may alternatively include an illuminating-light-controlling unit that prevents, if the occurrence of the pull-in effect has been detected by the pull-in-detection unit 130, highly intense light emitted from the light-source unit 101 from being applied to the object 113 (the eye of the examinee, for example). Furthermore, if the occurrence of the pull-in effect has been detected by the pull-in-detection unit 130, calibration for controlling the amount of light emitted from the light-source unit 101 may be performed. The method of changing the amount of light emitted from the light-source unit 101 varies with the type of the light source. If the light source is a MEMS-VCSEL, the amount of current to be injected into the active layer of the VCSEL is changed.

Clock-Generating Unit

The clock-generating unit 120 according to the first embodiment transmits a clock signal that allows the interference signal from the optical interferometric system 102 to be sampled at regular wave-number intervals. The clock-generating unit 120 includes an interferometer and a signal transmitter that detects the signal from the interferometer by using a photodetector or a balanced photodetector and then transmits a clock signal. The clock-generating unit 120 is hereinafter occasionally referred to as k-clock system.

When a portion of the light emitted from the light-source unit 101 is guided to the k-clock system 120, a clock signal (S1) that pulsates at a wave-number interval that is specific to the k-clock system 120 is generated in correspondence with changes in the wavelength of the light emitted from the light-source unit 101. The clock signal does not necessarily pulsate at exactly regular wave-number intervals.

The interference signal transmitted from the photodetection unit 103 to the information-acquiring unit 104 is sampled on the basis of the clock signal, whereby the interference signal is acquired at the above wave-number interval.

Photodetection Unit

The photodetection unit 103 according to the first embodiment is not specifically limited and only needs to be capable of converting the intensity of interfering light into the intensity of an electrical signal such as a voltage. The photodetection unit 103 converts information carried by the interference signal into information represented as a temporal waveform of a voltage received in the form of light.

Information-Acquiring Unit

The information-acquiring unit 104 acquires information on the object 113 on the basis of the temporal waveform representing the intensity of the interfering light received by the photodetection unit 103. Specifically, the arithmetic device included in the information-acquiring unit 104 performs frequency analysis such as Fourier transform, whereby information on the object 113 is acquired. The temporal waveform representing the intensity of the interfering light is sampled at regular frequency intervals (at regular wave-number intervals) on the basis of the clock signal transmitted from the clock-generating unit 120.

Light-Source Unit

The light-source unit 101 included in the OCT apparatus 100 according to the first embodiment is not specifically limited. The light-source unit 101 only needs to be capable of performing wavelength sweep by displacing the movable portion with an electrostatic force generated by the application of a voltage, and to have the problem described above. The light-source unit 101 according to the first embodiment may be of an external-resonator type, instead of being the MEMS-VCSEL described above. Exemplary external-resonator light sources include a swept light source. The swept light source includes a resonator comprising two reflectors. The resonator includes an optical-gain medium. One of the two reflectors is a half mirror and forms a Fabry-Perot (FP) resonator in combination with the other of the two reflectors. The half mirror is oscillated with an electrostatic force.

While the first embodiment concerns a case where the OCT apparatus 100 includes the pull-in-detection unit 130, the light-source unit 101 may include the pull-in-detection unit 130.

If the MEMS-VCSEL is a surface-emitting laser that emits light with the injection of an electric current into an active layer as described above, the occurrence of the pull-in effect may be detected by detecting the flow of a high current caused by an electrical short circuit between an upper reflector and an upper cladding layer. The high current can be detected by, for example, using an ammeter equipped with a current-controlling unit that drives the MEMS-VCSEL. If a high current is detected, the amount of current injection may be controlled by using the current-controlling unit.

The light-source unit 101 according to the first embodiment may be an optically pumped surface-emitting laser that emits light by applying light to an active layer. In that case, the pull-in-detection unit may be configured such that the pumping light reflected by one of the upper reflector and the lower reflector that is displaceable is detected and, if the reflected light is not in a predetermined state, it is determined that the pull-in effect is occurring. The reason for this is as follows. While the pull-in effect is occurring, one of the upper reflector and the lower reflector that is displaceable is assumed to be displaced by a larger amount than in the normal operation. Hence, for example, if pumping light is made to incident obliquely on the reflector, the path of the pumping light reflected by the reflector is changed. Such a change in the optical path at the reflection may be detected by, for example, directly detecting the change in the length of the optical path with an imaging device such as a camera. If the change in the length is out of a predetermined range, it is determined that the pull-in effect is occurring. For another example, the light reflected by the reflector may be made to incident on a light-receiving element, such as a photodiode, provided at a fixed position. In this case, if the optical path is changed and the intensity of the light detected by the light-receiving element is out of a predetermined range, it is determined that the pull-in effect is occurring.

For yet another example, pumping light may be made to incident on the reflector perpendicularly from above, and the time elapsed from when the pumping light is reflected by the reflector until when the reflected light returns to the position of emission along the same optical path may be measured. As described above, while the pull-in effect is occurring, the reflector is displaced by a large amount. Therefore, it takes longer for the reflected light to return to the position of emission than in the normal operation. This delay in the return time is detected. If the delay in the return time is out of a predetermined range, it is determined that the pull-in effect is occurring.

The predetermined range mentioned above will now be described. For example, letting the signal (the change in the optical path at the reflection or the delay in the return time of the reflected light) in the normal operation be a, and the dispersion in the signal measured within a predetermined period of time be a, any of the following ranges can be set: a range greater than or equal to $a+3\sigma$, a range greater than or equal to $a+5\sigma$, and a range greater than or equal to $a+7\sigma$. The range can be made close to the value a if the sensitivity of detection is desired to be increased, or far from the value a if an unwanted signal, such as noise, which may occur during the normal operation is desired to be reduced. That is, the range needs to be set appropriately in accordance with the purpose of detection.

Object

The object 113 in the first embodiment is an object of measurement performed by the OCT apparatus 100 according to the first embodiment, and the kind of the object 113 is not specifically limited. For example, the object 113 may be any of living organisms such as an eyeball, skin, a blood vessel, a tooth, and so forth.

Display Unit

In the OCT apparatus 100 according to the first embodiment, the information on the object 113 that is acquired by the information-acquiring unit 104 is a tomographic image. The OCT apparatus 100 may include the image display unit 119 that displays the tomographic image.

Applications

The OCT apparatus 100 according to the first embodiment is applicable to the fields of ophthalmology, dentistry, dermatology, and so forth and to the acquisition of tomographic images of any living bodies such as animals and human beings. Information on a living body in the form of a tomographic image implies not only a tomographic image of the living body but also numerical data necessary for the acquisition of the tomographic image.

The OCT apparatus 100 according to the first embodiment is particularly suitable for a case where the measurement object is the fundus of a human eyeball and information on the fundus in the form of a tomographic image is to be acquired.

The surface-emitting laser as the light-source unit 101 according to the first embodiment may be used as a light source for optical communications or optical measurement, as well as a light source for OCT.

Second Embodiment

An OCT apparatus according to a second embodiment of the present invention will now be described, focusing on differences from the first embodiment while omitting description of elements common to the first embodiment. FIG. 4 is a block diagram of an OCT apparatus according to the second embodiment.

A light-source unit 401 is a swept light source including a MEMS that is driven by an electrostatic force. Light emitted from the light-source unit 401 travels through a fiber (a solid line in FIG. 4) and enters an optical coupler 402, where the light is split into two portions. One of the portions as measuring light enters an OCT measurement system. The other portion enters a wave-number-acquiring interferometer 403.

The measuring light that has entered the measurement system enters an optical coupler 405, where the measuring light is split into object-measuring light and reference light.

The object-measuring light travels through a polarization controller 406 and a fiber-coupling lens 407 and is applied to a measurement object 408. A dotted line connecting the fiber-coupling lens 407 and the measurement object 408 in FIG. 4 represents the light traveling through the air. The reflected light (i.e., signal light) from the measurement object 408 enters the fiber-coupling lens 407 again and returns along the same path, i.e., a fiber system, into the optical coupler 405. In the optical coupler 405, the reflected light is split into two portions, one of which enters a fiber coupler 414 and the other of which travels through the optical coupler 402 and is fed back toward the light-source unit 401. The other portion of the reflected light, i.e., the feedback light, is mostly absorbed by an optical isolator (not illustrated) before reaching the light-source unit 401.

Meanwhile, the reference light travels through a polarization controller 409 and a fiber-coupling lens 410 into a spatial system and enters a reference mirror unit 411. The reference mirror unit 411 includes four 45° prism mirrors 412 and is capable of adjusting the optical-path length of the reference light. The reference light that has traveled through the reference mirror unit 411 further travels through a fiber-coupling lens 413 into a fiber system and enters the fiber coupler 414.

In the fiber coupler 414, the signal light and the reference light returning from the reference mirror unit 411 are coupled into an interference signal. The interference signal enters a balanced photodetector 415 and is detected by the balanced photodetector 415. The balanced photodetector 415 convers the interference signal into an electrical signal and transmits the electrical signal to a measuring-signal analog-digital converter (ADC) 416 (the flow of the electrical signal is represented by arrow-headed solid lines in FIG. 4). The measuring-signal ADC 416 converts the electrical signal into a digital data. The digital data is transmitted to a computer 417, where the digital data is processed.

The light that has been emitted from the light-source unit 401 and has entered the wave-number-acquiring interferometer 403 turns into interfering light intended for wave-number acquisition. The interfering light enters and is detected by a balanced photodetector 404, where the interfering light is converted into an electrical signal. The wave-number-acquiring interferometer 403 may be any of known interferometers such as a Michelson interferometer and a Mach-Zehnder interferometer. The electrical data obtained from the electrical signal is separated into a signal for the generation of an external clock that is to be used for the analog-digital conversion of the interference signal carrying the information on the measurement object 408 and a pull-in-checking signal to be used in the process of checking whether or not the pull-in effect is occurring.

The signal for the generation of an external clock is processed by an external-clock-generating unit 418, thereby turning into a clock signal. The clock signal is transmitted to the measuring-signal ADC 416 and is used as an external clock signal. The clock-generating unit 120 according to the first embodiment corresponds to a section including the wave-number-acquiring interferometer 403, the balanced photodetector 404, and the external-clock-generating unit 418 according to the second embodiment.

The pull-in-checking signal is first transmitted to a signal-shaping unit 419 and is shaped into a signal that is suitable for the checking of the occurrence of the pull-in effect. The signal-shaping unit 419 includes various analog electrical circuits and so forth. The pull-in-checking signal thus shaped is transmitted to a pull-in-checking-signal analog-digital converter (ADC) 420 and then to the computer 417, where the pull-in-checking signal is processed, and it is checked whether or not the pull-in effect is occurring. If it is determined that the pull-in effect is occurring, a command is transmitted to a handling mechanism 421 as a pull-in-handling unit, whereby the handling mechanism 421 is activated to handle the situation. Depending on the method of checking the occurrence of the pull-in effect, the signal-shaping unit 419 may be omitted and the signal may be directly transmitted to the pull-in-checking-signal ADC 420. The function of the pull-in-detection unit 130 according to the first embodiment is allocated to the computer 417 in the second embodiment.

In the second embodiment, a section from a point where the pull-in-checking signal is obtained through the separation of the electrical signal by the balanced photodetector 404, passing through the pull-in-checking-signal ADC 420, to the computer 417 where the occurrence of the pull-in effect is checked is defined as a pull-in-detecting mechanism. A section from the computer 417 that issues a command on the basis of the result of the check to the handling mechanism 421 that performs a handling process is defined as a pull-in-handling mechanism.

The above OCT apparatus may include a plurality of wave-number-acquiring interferometers 403. In that case, the plurality of interferometers 403 may have different optical-path lengths. Thus, a plurality of pull-in-detecting signals, to be described below, can be acquired. Alternatively, the optical-path length of the wave-number-acquiring interferometer 403 may be variable. In such a configuration also, two kinds of interfering light intended for wave-number acquisition can be obtained.

The OCT apparatus may include a plurality of light-source units 401.

FIG. 5 is a flowchart illustrating a process of determining whether or not the pull-in effect is occurring that is performed in the second embodiment. First, in step 501, the relationship between the signal intensity and the time elapsed is outputted for every specific number of times for which A-scan is performed (A-scan is a scan corresponding to a measurement in the depth direction of the measurement object 408). In the second embodiment. A-scan is performed two times for every single reciprocating sweep of the wavelength (each of a forward movement and a backward movement of the reflector corresponds to a single performance of A-scan). The criterion for determining whether or not the pull-in effect is occurring is whether or not the pull-in-checking signal obtained during a single reciprocating sweep of the wavelength has any portions where the intensity thereof is constant for over a certain period of time. That is, in step 502, whether or not the pull-in-checking signal has such a portion is checked. Note that A-scan may be performed only once for every single reciprocating sweep (only for forward or backward sweep) of the wavelength.

The criterion for determining whether or not the pull-in effect is occurring includes two factors, one of which is the period of time that is longer than a certain period of time, and the other of which is the signal output in which the signal intensity is constant. Referring to FIG. 6, the period of time will first be described. FIG. 6 is a schematic chart illustrating a displacement curve 601 of the reflector (movable portion) that is observed in a single reciprocating sweep of the wavelength in the normal operation, and an exemplary waveform of a pull-in-checking signal 602 corresponding to the displacement curve 601. As illustrated in FIG. 6, the pull-in-checking signal 602 becomes constant at each of portions corresponding to the peak and the bottoms of the displacement curve 601 even in the normal driving of the reflector. As the gradient of the displacement curve 601 becomes gentler, the period of time for which the pull-in-checking signal 602 remains constant (the period of time corresponding to the peak or the bottom of the displacement curve 601) tends to become longer. Particularly, at the peak and the two ends of the displacement curve 601 in FIG. 6, the period of time for which the pull-in-checking signal 602 remains constant tends to become longest. The threshold of the period of constant signal intensity that is intended for the determination of whether or not the operation is normal corresponds to the threshold of the period of constant signal intensity that is intended for the determination of whether or not the pull-in effect is occurring.

The threshold of the period of constant signal intensity that is intended for the determination of whether or not the pull-in effect is occurring can be set to a period longer than the longest one of the periods of constant signal intensity that are observed in the normal operation. Considering the dispersion σ(sec) in the period of constant signal intensity among a plurality of wavelength sweeps performed within a predetermined measurement time, the threshold can be set to about (longest period)+3σ(sec). If the threshold is set to about (longest period)+5σ(sec), the accuracy in the determination of whether or not the pull-in effect is occurring can be increased correspondingly.

Now, the threshold of the constant signal intensity will be described. The signal contains noise components. Therefore, a certain threshold of the constant signal intensity needs to be set. Here, letting the dispersion in the amplitude of noise contained in the signal acquired in a predetermined measurement time be σ, the signal intensity is regarded as being constant if it falls within a range of +/−5σ of the median or more preferably a range of +/−3σ of the median.

The above thresholds are only exemplary, and other thresholds may alternatively be employed.

With reference to the above thresholds, whether or not the pull-in effect is occurring is determined in step 503. In the second embodiment, if it is determined that the pull-in effect is occurring, a signal is transmitted to the power source of the light-source unit 401 so that the application of the voltage to the electrodes of the MEMS that has been displacing the movable portion is stopped in step 504.

While the second embodiment concerns a case where the waveform of the voltage for driving the reflector is sinusoidal, the waveform of the driving voltage may be in any other shape such as a sawtooth shape.

While the second embodiment concerns a case where the light-source unit 401 is kept on during both upward and downward displacements of the movable portion undergoing wavelength sweep, the light-source unit 401 may be kept on during only one of the upward and downward displacements or may not necessarily be kept on over the entire period of the displacement.

In the second embodiment, if the optical-path-length difference of the wave-number-acquiring interferometer 403 is variable, the state of interference of the signal can be changed. For example, if the optical-path-length difference of the wave-number-acquiring interferometer 403 is changed when the intensity of the interference signal is zero, the value of the constant portion of the signal can be changed to a finite value. Thus, whether the light-source unit 401 is off (if the light-source unit 401 is off, the value of the constant portion of the signal remains zero even after the optical-path-length difference of the wave-number-acquiring interferometer 403 is changed) or the pull-in effect is occurring can be determined.

In the second embodiment, the pull-in-checking-signal ADC 420 may be used as the measuring-signal ADC 416. In that case, since the measuring signal and the pull-in-checking signal are processed alternately by the same ADC, the measurement time increases. However, the number of components is reduced, which is an advantage.

Third Embodiment

An OCT apparatus according to a third embodiment of the present invention will now be described, focusing on differences from the first and second embodiments while omitting description of elements common to the first and second embodiments.

The third embodiment concerns another method of checking the occurrence of the pull-in effect that corresponds to step 502 according to the second embodiment illustrated in FIG. 5. The OCT apparatus, the mechanism of detecting the pull-in effect, and the mechanism of handling the pull-in effect that are employed in the third embodiment are the same as those employed in the first embodiment.

In the second embodiment, the checking of whether or not the pull-in effect is occurring is performed by detecting any portions of the pull-in-checking signal where the intensity is constant. That is, the signal data is read directly, in the third embodiment, the pull-in-checking signal is converted into data representing the amplitude.

FIG. 7 is a conceptual chart illustrating the principle of the checking of the occurrence of the pull-in effect that is employed in the third embodiment. A pull-in-checking signal 701 has a periodic shape when the pull-in effect is not occurring. The values of the amplitude of the pull-inchecking signal 701 can be interpreted into amplitude data 702. The amplitude data 702 in the lower part of FIG. 7 is generated on the basis of the difference in the value of the pull-in-checking signal 701 between the peak and the bottom. While the pull-in effect is occurring, the amplitude is zero as represented by the amplitude data 702. The pull-in effect continues to occur during a period of time for which the amplitude is zero. Hence, the occurrence of the pull-in effect can be detected by detecting the zero portion of the amplitude data 702.

Actually, the amplitude of the pull-in-checking signal 701 does not remain zero for a certain period of time because of noise or the like. Therefore, a specific threshold that determines whether or not the pull-in effect is occurring needs to be set, as in the second embodiment. In the third embodiment, the amplitude of the pull-in-checking signal 701 needs to be smaller than a predetermined value but to be larger than the amplitude of noise. Hence, if the amplitude falls within such a range, it is determined that the pull-in effect is occurring. For example, letting the amplitude of the pull-in-checking signal 701 be a and the dispersion in the amplitude of noise contained in the signal acquired during a predetermined measurement time be $\sigma$, the threshold of the above range can be set as follows: |a| is smaller than $3\sigma$, or preferably |a| is smaller than $5\sigma$, or more preferably |a| is smaller than $7\sigma$ (|| indicates that the value enclosed is an absolute value). The larger the threshold, the better in terms of distinguishing from aliases, such as noise, which may be included accidentally in the signal. However, if the threshold is too large, the amplitude of the pull-in-checking signal 701 in the normal operation may be regarded as the pull-in effect. To avoid such a situation, the threshold of the range can be set as follows: |a| is smaller than $A_{min}-3\sigma$, |a| is smaller than $A_{min}-5\sigma$, or |a| is smaller than $A_{min}-7\sigma$, where denotes the minimum value of the amplitude in the normal operation, and $\sigma$ denotes the dispersion thereof. The actual threshold needs to be determined individually within a range that complies with the above principle.

In the above method according to the third embodiment, since the amplitude of the signal is checked, there is no need to set any threshold concerning the period of time of the signal that is set in the second embodiment. Accordingly, the number of conditions for the checking can be reduced. To check the amplitude (the difference between the value at the peak and the value at the bottom) of the signal, for example, software such as a known computer program for signal processing implemented by electrical circuits can be used.

Fourth Embodiment

An OCT apparatus according to a fourth embodiment of the present invention will now be described, focusing on differences from the first to third embodiments while omitting description of elements common to the first to third embodiments.

The fourth embodiment concerns yet another method of checking whether or not the pull-in effect is occurring that corresponds to step 502 according to the second embodiment illustrated in FIG. 5. The OCT apparatus according to the fourth embodiment has the same configuration as that illustrated in FIG. 4. Hence, the following description is based on FIG. 4.

In the fourth embodiment, the pull-in-checking signal is processed and differentiated in advance by the signal-shaping unit 419, whereby, before the signal is transmitted to the computer 417, the pull-in-checking signal is converted into a form that is suitable for checking any portions of the signal where the amplitude is zero. Thus, the step of checking whether or not the pull-in effect is occurring can be performed quickly while the step of checking the amplitude of the signal by the computer 417 is skipped. Consequently, the measurement time is reduced. The signal-shaping unit 419 according to the fourth embodiment includes a differentiating circuit and so forth.

The steps of data processing performed in the computer 417 are the same as those employed in the second embodiment illustrated in FIG. 5, except that the data invoked in step 501 is the signal that has been shaped in advance by the signal-shaping unit 419 as described above. The step of checking whether or not the pull-in effect is occurring that is performed by the computer 417 is the same as that employed in the second embodiment. The step of handling the pull-in effect that is performed after the check is also the same as that employed in the second embodiment.

Fifth Embodiment

An OCT apparatus according to a fifth embodiment of the present invention will now be described, focusing on differences from the first to fourth embodiments while omitting description of elements common to the first to fourth embodiments.

The fifth embodiment concerns yet another method of checking whether or not the null in effect is occurring that corresponds to step 502 according to the second embodiment illustrated in FIG. 5. The fifth embodiment also differs from the second embodiment in the method of handling the pull-in effect that corresponds to step 504, which will also be discussed below.

FIG. 8 is a schematic diagram illustrating the OCT apparatus according to the fifth embodiment. In the OCT apparatus according to the fifth embodiment, a signal generated by a wave-number-acquiring interferometer 803 is not separated. The signal is used as an external clock signal intended for the acquisition of a measuring interference signal. This is a typical OCT apparatus according to the fifth embodiment that includes a wave-number-acquiring interferometer. The handling mechanism 421, illustrated in FIG. 4, activated at the detection of the occurrence of the pull-in effect corresponds to a shutter 819 in the fifth embodiment. The shutter 819 shields a measurement object 808 from the light.

Referring to FIG. 9, a method of checking whether or not the pull-in effect is occurring according to the fifth embodiment will now be described. In the fifth embodiment, the signal for the generation of an external clock that is outputted from the wave-number-acquiring interferometer 803 is also used as the pull-in-checking signal.

An upper part of FIG. 9 illustrates a curve 901 representing the interference signal that is outputted from the wave-number-acquiring interferometer 803 and from which a clock signal as an external clock that pulsates at regular wave-number intervals is acquired. In the fifth embodiment, the clock signal pulsating at regular wave-number intervals is represented by extracting points 902 where the curve 901 representing the interference signal intersects the horizontal axis representing the value of zero. As can be seen from the extracted points 902 where the interference signal becomes zero, while the pull-in effect is occurring (during a period in which the voltage represented by the curve 901 is constant), no points 902 are observed and the interval between adjacent points is longer than that observed in the normal operation. If such a period is detected, it is determined that the pull-in effect is occurring. In the fifth embodiment, the clock signal is acquired by detecting the points of time where the signal from the wave-number-acquiring interferometer 803 becomes zero. Alternatively, the clock signal may be acquired by detecting the points of time where the signal becomes the maximum value (the peak) and the minimum value (the bottom).

In the fifth embodiment also, a threshold that determines whether or not the pull-in effect is occurring needs to be set. In the fifth embodiment, only the interval between pulses of the clock signal needs to be set. Specifically, the pull-in effect is regarded as occurring if the interval between pulses of the clock signal is longer than a predetermined interval. The predetermined interval corresponds to the period during which the pull-in effect is occurring, and can therefore be set to be longer than the longest one of the intervals between pulses of the clock signal that are observed in the normal operation, because of the same reason as for the second embodiment in which the period of time for which the signal intensity is constant is used as a factor for the determination. Furthermore, considering the dispersion σ in the interval between pulses of the clock signal among a plurality of wavelength sweeps performed within a predetermined measurement time, the threshold can be set to (longest interval between pulses of the clock signal)+3σ or (longest interval between pulses of the clock signal)+5σ.

The signal actually used in performing the above check in a computer 817 is the above external clock signal or the measuring interference signal itself that is acquired by using the external clock. The check is performed on the basis of the interval between pieces of time-series data represented by them.

If it is determined that the pull-in effect is occurring as described above, the computer 817 issues a command for immediately shutting the shutter 819. Thus, a situation where highly intense light is applied to a measurement object 808 (the examinee) can be ended immediately. In the fifth embodiment, the shutter 819 is provided in front of the measurement object 808. Alternatively, the shutter 819 may be provided in front of a light-emitting portion of a light-source unit 801, more specifically, in front of a light source chip built in a light source package. Moreover, the shutter 819 may be a mechanical shutter, or an electronic shutter, such as liquid crystal, including a mechanism of controlling the transmittance.

In the OCT apparatus according to the fifth embodiment, the above check can be performed with a typical configuration without the need for separating the signal in the wave-number-acquiring interferometer 803. Hence, the configuration of the OCT apparatus can be simplified.

In the fifth embodiment, whether or not the pull-in effect is occurring is checked on the basis of the interval between pulses of the clock signal that is outputted from an external-clock-generating unit 818. Alternatively, the signal that is yet to be converted into an external clock signal by the external-clock-generating unit 818 may be used for the check. For example, the signal obtained immediately after the detection of zero-intensity points in the external-clock-generating unit 818 and that is yet to be converted into a clock signal to be transmitted to a measuring-signal ADC 816 may be supplied to the computer 817. To do so, the wiring line from the external-clock-generating unit 818 is made to branch off to the computer 817 so that the signal is supplied to the computer 817 as a pull-in-checking signal that is separate from the external clock, as in the first embodiment.

The elements denoted by reference numerals 801 to 815 illustrated in FIG. 8 correspond to the elements denoted by reference numerals 401 to 415 illustrated in FIG. 4, and description thereof is omitted herein.

Sixth Embodiment

An OCT apparatus according to a sixth embodiment of the present invention will now be described, focusing on differences from the first to fifth embodiments while omitting description of elements common to the first to fifth embodiments.

The sixth embodiment employs the same process of detecting the occurrence of the pull-in effect and stopping the application of the voltage to the MEMS as that employed by the second embodiment, but is characterized in that a process of recovering the OCT apparatus is performed after the step of stopping the application of the voltage to the MEMS. Specifically, a signal from the light source is checked, and problems, if any, are corrected. In such a recovering process performed after the occurrence of the pull-in effect, the characteristics of the light source that might have been changed because of the pull-in effect are examined and calibrated by the OCT apparatus itself to a maximum extent, whereby the OCT apparatus recovers its operable state.

FIG. 10 is a flowchart basically illustrating the recovering process performed after the occurrence of the pull-in effect according to the sixth embodiment. The process of detecting and handling the pull-in effect that is performed before the recovering process is the same as that illustrated in FIG. 5.

In the process illustrated in FIG. 10, after the occurrence of the pull-in effect has been detected and the application of the voltage to the MEMS is stopped in step 1004, the process proceeds to the recovering process. First, whether or not there is any optical output from the light source is checked in step 1001. If the pull-in effect occurs, a high current may flow through the light-source element. Consequently, the light-source element may be damaged. Therefore, in the recovering process, whether or not the light-source element is damaged is checked first. In the checking step, the optical output from the light-source element is monitored by using a photodetector (not illustrated) provided near the light-source element or a detector (not illustrated) configured to monitor the light derived from the OCT measurement light. If the light source includes an optically pumped light-source element, the checking step may be omitted. If there is no optical output from the light source in step 1001 illustrated in FIG. 10, an indication notifying that the light-source element needs to be replaced is displayed on the image display unit of the OCT apparatus, for example, in step 1002. If there is any optical output, the light source is driven again in step 1003 and the interference signal is checked in step 1005. If the pull-in effect occurs, one of the driving electrodes included in the MEMS is significantly pulled toward the other driving electrode. Consequently, the driving electrode may be deformed, and the characteristics (the speed, the range, the amplitude, and so forth of the MEMS) of the light source may change. In such a case, the interference signal obtained in the OCT apparatus may also change. Consequently, the way the resulting tomographic image appears (the contrast, the resolution, and so forth of the tomographic image) may change. Moreover, the light-emission characteristic of the light source may change. In step 1005, whether or not the interference signal is the same as that obtained before the occurrence of the pull-in effect is checked with reference to a predetermined reference sample. The reference sample may be an artificial eye sample including a mirror and an artificial fundus. The interference signal before the occurrence of the pull-in effect (the interference signal obtained when there is no pull-in effect) is obtained in advance (and stored, for example, in a storage device). If an interference signal that is the same as the interference signal obtained before the occurrence of the pull-in effect is obtained in step 1005, it is determined that the interference signal is normal, that is, there are no changes between the states of the light source before and after the occurrence of the pull-in effect. Hence, it is determined that the OCT apparatus is normally operable. If the interference signal obtained after the occurrence of the pull-in effect is different from the interference signal obtained before the occurrence of the pull-in effect, it is determined that some characteristics of the light source have changed. Then, the process proceeds to step 1006, where the conditions for driving the light source are calibrated. In step 1006, the signal obtained from the k-clock system is checked first. Specifically, the number of and the interval between points of the signal from the k-clock system are checked. If the differences in the values of such items of the signal from the values obtained before the occurrence of the pull-in effect are out of predetermined ranges, it is determined that the conditions for driving the MEMS have changed. Accordingly, the temporal waveform of the voltage for driving the MEMS is calibrated such that the values of the above items become the same as those obtained before the occurrence of the pull-in effect. If there are no changes in the signal from the k-clock system, this calibration step is skipped. After the calibration, basic data on the light source are acquired for each of the sampling points determined by the k-clock system using data of a tomographic image. Data to be acquired here are the current-to-optical-output characteristic and the current-to-voltage characteristic of the light source. The data are acquired for each of all sampling points determined by the k-clock system on a certain spot in the tomographic image of the reference sample. On the basis of the data thus acquired, the current to be injected into (the voltage to be applied to) the light-emitting portion is calibrated such that the intensity of the interference signal at each of the sampling points become the same as that obtained before the occurrence of the pull-in effect. If the data can be calibrated successfully in such a manner, the process proceeds to step 1005, where the interference signal is checked again. If the differences in the data from those obtained before the occurrence of the pull-in effect are too great to correct only by the calibration of the voltage for driving the light source (the light-emitting portion and the MEMS), it is determined that the data are not calibratable. Then, an indication notifying that the light-source element needs to be replaced is displayed on the image display unit of the OCT apparatus, for example, in step 1002. It is preferable that the calibration of the light source on the k-clock sampling points be performed on a plurality of spots for measurement in the reference sample.

The calibration of the voltage for driving the MEMS and the calibration of the current to be injected into (the voltage to be applied to) the light-emitting portion may be performed by a control unit that controls the voltage for driving the MEMS and a control unit that controls the current to be injected into the light-emitting portion, respectively. Alternatively, a control unit that performs the calibrations may be provided separately.

EXAMPLE

An example of the present invention will now be described. The present invention is not limited to the following example, and the design and configuration thereof may be changed appropriately.

Example 1

An OCT apparatus according to Example 1 of the present invention will now be described. The OCT apparatus according to Example 1 is the same as the OCT apparatus illustrated in FIG. 4, except that the signal-shaping unit 419 is omitted.

In Example 1, if it is determined that the pull-in effect is occurring, the handling mechanism 421 sets the voltage applied to the reflector of the MEMS to zero by controlling the voltage for driving the light-source unit 401.

In Example 1, the wavelength is swept from 1030 nm to 1090 nm. The MEMS includes a beam that itself functions as a semiconductor multilayer-film reflector. In the measurement, the MEMS is driven sinusoidally at a sweep frequency of 100 kHz, normally. The multilayer-film reflector is made of two kinds of semiconductors, which are GaAs and AlGaAs. The sweep is performed at a frequency lower than the resonance frequency of the reflector of the MEMS. A GaAs-based compound semiconductor laser including an InGaAs active layer is employed as the half VCSEL. In Example 1, a semiconductor optical amplifier (SOA) for amplifying the optical output is provided on the downstream side of the MEMS-VCSEL. A combination of the SOA and a light source is regarded as the light-source unit 401. The optical output of the light-source unit 401 is 25 mW.

The optical couplers 402, 405, and 414 have respective splitting ratios of 95 to 5 (95 is for the side of the measurement system), 70 to 30 (30 is for the side of the measurement object 408), and 50 to 50. The wave-number-acquiring interferometer 403 is a Machzehnder interferometer. The clock signal generated by the measuring-signal ADC 416 is at 500 MHz. The clock signal generated by the pull-in-checking-signal ADC 420 is at 2.0 GHz.

The pull-in-checking signal obtained after the split is directly converted into a digital signal by the pull-in-checking-signal ADC 420 and is subjected to the checking of the occurrence of the pull-in effect performed by the computer 417.

In the OCT apparatus according to any of the embodiments of the present invention, the occurrence of the pull-in effect in the light-source unit can be detected. If the occurrence of the pull-in effect is detected, such a state affected by the pull-in effect can be changed to a state free of the pull-in effect or the influence of the pull-in effect upon the OCT apparatus can be suppressed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-135391, filed Jun. 30, 2014, which is hereby incorporated by reference herein in its entirety.

The invention claimed is:

1. An optical-coherence-tomography apparatus comprising:
a light-source unit configured to emit light while changing a wavelength of the light;
an optical interferometric system configured to split the light from the light-source unit into illuminating light to be applied to an object and reference light, and to generate interfering light both from the illuminating light reflected by the object and the reference light;

a photodetection unit configured to receive the interfering light; and an information-acquiring unit configured to acquire information on the object from the interfering light received by the photodetection unit, wherein the light-source unit includes a movable portion that is displaceable with an electrostatic force, the movable portion being used in performing wavelength sweep, and wherein the optical-coherence-tomography apparatus further includes a pull-in-detection unit configured to detect whether or not a pull-in effect is occurring on the movable portion of the light-source unit.

2. The optical-coherence-tomography apparatus according to claim 1, further comprising:

a clock-generating unit configured to acquire an interference signal having peaks appearing at regular wave-number intervals from the light emitted from the light-source unit, and to generate, with reference to the interference signal, a clock signal pulsating at the regular wave-number intervals, wherein the pull-in-detection unit detects the occurrence of the pull-in effect with reference to the interference signal or the clock signal.

3. The optical-coherence-tomography apparatus according to claim 1, wherein the pull-in-detection unit determines that the pull-in effect is occurring if an intensity of the interference signal or the clock signal is constant for a predetermined period of time.

4. The optical-coherence-tomography apparatus according to claim 1, wherein the pull-in-detection unit determines that the pull-in effect is occurring if an amplitude of the interference signal is a predetermined value or smaller.

5. The optical-coherence-tomography apparatus according to claim 1, wherein the pull-in-detection unit determines that the pull-in effect is occurring if an interval between regular wave-number points of the clock signal is longer than a predetermined period of time.

6. The optical-coherence-tomography apparatus according to claim 1, wherein the pull-in-detection unit determines that the pull-in effect is occurring if a derivative of the interference signal in the clock-generating unit is zero for a predetermined period of time.

7. The optical-coherence-tomography apparatus according to claim 1, wherein the light-source unit is a surface-emitting laser including a lower reflector, an active layer, and an upper reflector that are stacked in that order, wherein an air gap is provided between the active layer and the upper reflector, and wherein the wavelength of the light emitted from the surface-emitting laser is changed by displacing at least one of the upper reflector and the lower reflector in an optical-axis direction of the reflector.

8. The optical-coherence-tomography apparatus according to claim 7, wherein the surface-emitting laser emits light when pumping light is applied to the active layer.

9. The optical-coherence-tomography apparatus according to claim 8, wherein the pull-in-detection unit detects the occurrence of the pull-in effect with reference to the pumping light reflected by the at least one of the upper reflector and the lower reflector that is displaced.

10. The optical-coherence-tomography apparatus according to claim 7, wherein the surface-emitting laser includes a current-controlling unit configured to inject a current into the active layer, and emits light when the current is injected into the active layer from the current-controlling unit.

11. The optical-coherence-tomography apparatus according to claim 1, further comprising a voltage-controlling unit, wherein, if the voltage-controlling unit has received a signal from the pull-in-detection unit, the voltage-controlling unit controls a voltage with which the movable portion is displaced.

12. The optical-coherence-tomography apparatus according to claim 1, further comprising an illuminating-light-controlling unit, wherein, if the illuminating-light-controlling unit has received a signal from the pull-in-detection unit, the illuminating-light-controlling unit prevents the light emitted from the light-source unit from being applied to the object.

13. The optical-coherence-tomography apparatus according to claim 1, further comprising an illuminating-light-controlling unit, wherein, if the illuminating-light-controlling unit has received a signal from the pull-in-detection unit, the illuminating-light-controlling unit controls an amount of light to be emitted from the light-source unit.

14. A surface-emitting laser comprising:

a lower reflector, an active layer, and an upper reflector that are stacked in that order, wherein an air gap is provided between the active layer and the upper reflector, wherein a wavelength of the light emitted from the surface-emitting laser is changed by displacing at least one of the upper reflector and the lower reflector in an optical-axis direction of the reflector, and wherein the surface-emitting laser further includes a detecting unit configured to detect whether or not the pull-in effect is occurring on the at least one of the upper reflector and the lower reflector that is displaced.

15. The optical-coherence-tomography apparatus according to claim 1, wherein the optical-coherence-tomography apparatus is configured to notify information regarding to a state of the light-source unit.

16. The optical-coherence-tomography apparatus according to claim 1, wherein the optical-coherence-tomography apparatus is configured to display error message on an image display unit of the optical-coherence-tomography apparatus when a signal is output from the pull-in-detection unit.

17. The optical-coherence-tomography apparatus according to claim 1, wherein the optical-coherence-tomography apparatus is configured to notify that the light-source unit needs to be replaced.

* * * * *